United States Patent
Kim et al.

(10) Patent No.: US 7,785,572 B2
(45) Date of Patent: Aug. 31, 2010

(54) METHOD AND DEVICE FOR TEETH WHITENING USING A DRY TYPE ADHESIVE

(75) Inventors: Ji-Young Kim, Daejeon (KR); Jong-Ho Kim, Daejeon (KR); Sug-Youn Chang, Daejeon (KR); Sei-Young Yun, Daejeon (KR); An-gi Choi, Daejeon (KR)

(73) Assignee: LG Household and Health Care Ltd., Daejeon (KR)

( * ) Notice: Subject to any disclaimer, the term of this patent is extended or adjusted under 35 U.S.C. 154(b) by 651 days.

(21) Appl. No.: 10/856,468

(22) Filed: May 28, 2004

(65) Prior Publication Data

US 2004/0219111 A1    Nov. 4, 2004

Related U.S. Application Data

(63) Continuation-in-part of application No. 10/445,589, filed on May 27, 2003, now Pat. No. 6,780,401, which is a continuation of application No. 10/049,817, filed as application No. PCT/KR01/00207 on Feb. 13, 2001, now Pat. No. 6,682,721.

(30) Foreign Application Priority Data

Mar. 17, 2000    (KR) ............................... 2000-13636
Dec. 8, 2000    (KR) ............................... 2000-74599

(51) Int. Cl.
*A61K 8/00* (2006.01)
*A61K 8/22* (2006.01)

(52) U.S. Cl. .......................... 424/53; 424/49; 424/443; 424/435; 424/447; 424/448; 424/449

(58) Field of Classification Search .................. 424/53, 424/49, 448

See application file for complete search history.

(56) References Cited

U.S. PATENT DOCUMENTS

| | | | |
|---|---|---|---|
| 4,517,173 A | 5/1985 | Kizawa et al. | |
| 4,696,757 A | 9/1987 | Blank et al. | |
| 4,713,243 A | 12/1987 | Schiraldi et al. | |
| 4,728,291 A | 3/1988 | Golub | |
| 4,741,700 A | 5/1988 | Barabe | |
| 4,741,941 A | 5/1988 | Englebert et al. | |
| 4,786,253 A | 11/1988 | Morais | |
| 4,788,052 A * | 11/1988 | Ng et al. ........................ 424/53 | |
| 4,799,888 A | 1/1989 | Golub | |
| 4,812,308 A | 3/1989 | Winston et al. | |
| 4,839,156 A | 6/1989 | Ng et al. | |
| 4,839,157 A | 6/1989 | Ng et al. | |
| RE33,093 E | 10/1989 | Schiraldi et al. | |
| 4,891,211 A | 1/1990 | Winston | |
| 4,895,721 A | 1/1990 | Drucker | |
| 4,900,552 A | 2/1990 | Sanvordeker et al. | |
| 4,900,554 A | 2/1990 | Yanagibashi et al. | |
| 4,919,615 A | 4/1990 | Croll | |
| 4,933,182 A | 6/1990 | Higashi et al. | |
| 4,983,379 A | 1/1991 | Schaeffer | |
| 4,983,380 A | 1/1991 | Yarborough | |
| 5,000,940 A | 3/1991 | Staples et al. | |
| 5,008,106 A | 4/1991 | Merianos et al. | |
| 5,009,885 A | 4/1991 | Yarborough | |
| 5,032,178 A | 7/1991 | Cornell | |
| 5,041,280 A | 8/1991 | Smigel | |
| 5,055,287 A | 10/1991 | Kessler | |
| 5,059,417 A | 10/1991 | Williams et al. | |
| 5,084,268 A | 1/1992 | Thaler | |
| 5,098,303 A | 3/1992 | Fischer | |
| 5,110,583 A | 5/1992 | Sampathkumar | |
| 5,122,365 A | 6/1992 | Murayama | |
| 5,128,122 A | 7/1992 | Cerami et al. | |
| 5,130,124 A | 7/1992 | Merianos et al. | |
| 5,166,233 A | 11/1992 | Kuroya et al. | |
| 5,171,564 A | 12/1992 | Nathoo et al. | |
| RE34,196 E | 3/1993 | Munro | |
| 5,192,532 A | 3/1993 | Guay et al. | |
| 5,208,010 A | 5/1993 | Thaler | |
| 5,217,710 A | 6/1993 | Williams et al. | |

(Continued)

FOREIGN PATENT DOCUMENTS

GB    2108841 A    5/1983

(Continued)

OTHER PUBLICATIONS

Supplementary European Search Report for EP 01 90 6382, (corresponding EP application for parent application PCT/KR01/00207.

(Continued)

*Primary Examiner*—Frederick Krass
*Assistant Examiner*—Lezah W Roberts
(74) *Attorney, Agent, or Firm*—Fox Rothschild LLP; Gerard P. Norton; Shahnam Sharareh

(57) ABSTRACT

A dry type adhesive device for teeth whitening in which a peroxide tooth whitening agent is stabilized is disclosed. The dry type adhesive device for tooth whitening comprises a matrix type adhesive layer and a backing layer wherein the adhesive layer contains a peroxide as a teeth whitening agent and a hydrophilic glassy polymer as a base polymer so that the hydrophilic glassy polymer provides strong adhesion to teeth when hydrated at the enamel layer of the teeth in the moist oral cavity and the whitening agent is released. In particular, although the dry type adhesive device is touched with the hands or contact the skin during attaching to the teeth prior to hydration, no stickiness and releasing of the whitening agent takes place, thus being safe. In addition, since the dry type patch has strong adhesive strength to the teeth and excellent adhesion maintenance after being hydrated and attached to the teeth, it can remain attached to the teeth for a long time and thus exhibits excellent whitening effect even low concentrations of a whitening agent. Furthermore, the dry type adhesive device can provide excellent whitening within a short period of time.

36 Claims, No Drawings

U.S. PATENT DOCUMENTS

| | | | |
|---|---|---|---|
| 5,234,342 A | 8/1993 | Fischer | |
| 5,234,957 A * | 8/1993 | Mantelle | 514/772.6 |
| 5,240,415 A | 8/1993 | Haynie | |
| 5,256,402 A | 10/1993 | Prencipe et al. | |
| 5,279,816 A | 1/1994 | Church et al. | |
| 5,281,412 A | 1/1994 | Lukacovic et al. | |
| 5,290,566 A | 3/1994 | Schow et al. | |
| 5,292,502 A | 3/1994 | Burke et al. | |
| 5,302,375 A | 4/1994 | Viscio | |
| 5,310,563 A | 5/1994 | Curtis et al. | |
| 5,326,685 A | 7/1994 | Gaglio et al. | |
| 5,332,576 A | 7/1994 | Mantelle | |
| 5,340,314 A | 8/1994 | Tarvis | |
| 5,340,581 A | 8/1994 | Tseng et al. | |
| 5,348,734 A | 9/1994 | Ratcliff | |
| 5,366,285 A | 11/1994 | Borgen et al. | |
| 5,372,802 A | 12/1994 | Barrows et al. | |
| 5,376,006 A | 12/1994 | Fischer | |
| 5,380,198 A | 1/1995 | Suhonen | |
| 5,401,495 A | 3/1995 | Murayama | |
| 5,409,631 A | 4/1995 | Fischer | |
| 5,425,953 A | 6/1995 | Sinitov et al. | |
| 5,437,858 A | 8/1995 | Hungerbach et al. | |
| 5,438,076 A | 8/1995 | Friedman et al. | |
| 5,505,956 A | 4/1996 | Kim et al. | |
| 5,536,285 A | 7/1996 | Isaksson et al. | |
| 5,560,379 A | 10/1996 | Pieczenik | |
| 5,565,190 A | 10/1996 | Santalucia et al. | |
| 5,575,654 A | 11/1996 | Fontenot | |
| 5,611,687 A | 3/1997 | Wagner | |
| 5,614,174 A | 3/1997 | Hsu et al. | |
| 5,620,322 A | 4/1997 | Lococo | |
| 5,626,866 A | 5/1997 | Ebert et al. | |
| 5,631,000 A | 5/1997 | Pellico et al. | |
| 5,631,055 A | 5/1997 | Vines et al. | |
| 5,639,445 A | 6/1997 | Curtis et al. | |
| 5,648,064 A | 7/1997 | Gaffar et al. | |
| 5,683,680 A | 11/1997 | Santalucia et al. | |
| 5,689,182 A | 11/1997 | Togo et al. | |
| 5,700,478 A | 12/1997 | Biegajski et al. | |
| 5,707,611 A | 1/1998 | Ikemura et al. | |
| 5,707,736 A | 1/1998 | Levy et al. | |
| 5,713,738 A | 2/1998 | Yarborough | |
| 5,718,886 A | 2/1998 | Pellico | |
| 5,723,132 A | 3/1998 | Tseng et al. | |
| 5,725,843 A | 3/1998 | Fischer | |
| 5,746,598 A | 5/1998 | Fischer | |
| 5,766,574 A | 6/1998 | Christina-Beck et al. | |
| 5,770,105 A | 6/1998 | Fischer | |
| 5,770,182 A | 6/1998 | Fischer | |
| 5,776,437 A | 7/1998 | Burgess et al. | |
| 5,785,527 A | 7/1998 | Jensen et al. | |
| 5,785,957 A | 7/1998 | Losee et al. | |
| 5,814,303 A | 9/1998 | Williams et al. | |
| 5,814,304 A | 9/1998 | Wong et al. | |
| 5,820,822 A | 10/1998 | Kross | |
| 5,820,852 A | 10/1998 | Burgess et al. | |
| 5,820,854 A | 10/1998 | Glandorf | |
| 5,846,570 A | 12/1998 | Barrow et al. | |
| 5,849,269 A | 12/1998 | Burgess et al. | |
| 5,851,514 A | 12/1998 | Hassan et al. | |
| 5,855,875 A | 1/1999 | Williams et al. | |
| 5,858,332 A | 1/1999 | Jensen et al. | |
| 5,863,202 A | 1/1999 | Fontenot et al. | |
| 5,879,691 A | 3/1999 | Sagel et al. | |
| 5,885,553 A | 3/1999 | Michael | |
| 5,885,554 A | 3/1999 | Michael et al. | |
| 5,891,453 A | 4/1999 | Sagel et al. | |
| 5,894,017 A | 4/1999 | Sagel et al. | |
| 5,902,568 A | 5/1999 | Ryles et al. | |
| 5,908,614 A | 6/1999 | Montgomery | |
| 5,914,118 A | 6/1999 | Yamamura et al. | |
| 5,915,969 A | 6/1999 | Linden | |
| 5,922,307 A | 7/1999 | Montgomery | |
| 5,928,628 A | 7/1999 | Pellico | |
| 5,932,193 A | 8/1999 | Lopez et al. | |
| 5,945,032 A | 8/1999 | Breitenbach et al. | |
| 5,980,249 A | 11/1999 | Fontenot | |
| 5,985,249 A | 11/1999 | Fischer | |
| 5,989,526 A | 11/1999 | Aaslyng et al. | |
| 5,989,569 A | 11/1999 | Dirksing et al. | |
| 6,007,795 A | 12/1999 | Masterman et al. | |
| 6,017,515 A | 1/2000 | van den Bosch | |
| 6,022,528 A | 2/2000 | Waterfield et al. | |
| 6,030,222 A | 2/2000 | Tarver | |
| 6,036,493 A | 3/2000 | Sharma | |
| 6,036,943 A | 3/2000 | Fischer | |
| 6,045,811 A | 4/2000 | Dirksing et al. | |
| 6,072,100 A | 6/2000 | Mooney et al. | |
| 6,080,811 A | 6/2000 | Schehlmann et al. | |
| 6,083,421 A | 7/2000 | Huang et al. | |
| 6,086,855 A | 7/2000 | Fischer | |
| 6,096,328 A | 8/2000 | Sagel et al. | |
| 6,106,293 A | 8/2000 | Wiesel | |
| 6,106,812 A | 8/2000 | Prencipe et al. | |
| 6,110,446 A | 8/2000 | Prencipe et al. | |
| 6,121,213 A | 9/2000 | Vergara et al. | |
| 6,136,297 A | 10/2000 | Sagel et al. | |
| 6,149,895 A | 11/2000 | Kutsch | |
| 6,155,832 A | 12/2000 | Wiesel | |
| 6,174,516 B1 | 1/2001 | Curtis et al. | |
| 6,190,689 B1 | 2/2001 | Hoffmann et al. | |
| 6,197,331 B1 | 3/2001 | Lerner et al. | |
| 6,221,341 B1 | 4/2001 | Montgomery | |
| 6,241,973 B1 | 6/2001 | Rinne | |
| 6,274,122 B1 | 8/2001 | McLaughlin | |
| 6,277,458 B1 | 8/2001 | Dirksing et al. | |
| 6,280,708 B1 | 8/2001 | Ryles et al. | |
| 6,284,152 B1 | 9/2001 | Kross | |
| 6,290,934 B1 | 9/2001 | Kramer et al. | |
| 6,290,935 B1 | 9/2001 | Masters et al. | |
| 6,306,370 B1 | 10/2001 | Jensen et al. | |
| 6,309,622 B1 | 10/2001 | Watkins | |
| 6,309,625 B1 | 10/2001 | Jensen et al. | |
| 6,312,666 B1 | 11/2001 | Oxman et al. | |
| 6,312,670 B1 | 11/2001 | Montgomery | |
| 6,312,671 B1 | 11/2001 | Jensen et al. | |
| 6,319,510 B1 | 11/2001 | Yates | |
| 6,322,773 B1 | 11/2001 | Montgomery | |
| 6,322,774 B1 | 11/2001 | Jensen et al. | |
| 6,325,997 B1 | 12/2001 | Christopfel | |
| 6,331,291 B1 | 12/2001 | Glace et al. | |
| 6,331,292 B1 | 12/2001 | Montgomery | |
| 6,342,206 B1 | 1/2002 | Gopalkrishnan et al. | |
| 6,348,187 B1 | 2/2002 | Pan et al. | |
| 6,350,437 B1 | 2/2002 | Pasetti et al. | |
| 6,350,438 B1 | 2/2002 | Witt et al. | |
| 6,365,134 B1 | 4/2002 | Orlowski et al. | |
| 6,368,576 B1 | 4/2002 | Jensen et al. | |
| 6,375,933 B1 | 4/2002 | Subramanyam et al. | |
| 6,379,653 B1 | 4/2002 | Aaslyng et al. | |
| 6,391,283 B1 | 5/2002 | Jensen et al. | |
| 6,391,286 B1 | 5/2002 | Mitra et al. | |
| 6,403,060 B1 | 6/2002 | Bornstein et al. | |
| 6,409,992 B1 | 6/2002 | Kleinberg et al. | |
| 6,409,993 B1 | 6/2002 | Jensen et al. | |
| 6,409,994 B1 | 6/2002 | Dahlin | |
| 6,413,502 B1 | 7/2002 | Bornstein et al. | |
| 6,419,902 B1 | 7/2002 | Wright | |
| 6,419,905 B1 | 7/2002 | Alvarez Hernandez | |
| 6,419,906 B1 | 7/2002 | Xu et al. | |
| 6,423,300 B1 | 7/2002 | Kleinberg et al. | |
| 6,435,873 B1 | 8/2002 | Burgio | |
| 6,440,396 B1 | 8/2002 | McLaughlin | |

| | | |
|---|---|---|
| 6,440,749 B1 | 8/2002 | Cerami et al. |
| 6,447,757 B1 | 9/2002 | Orlowski et al. |
| 6,457,469 B1 | 10/2002 | Mueller et al. |
| 6,458,340 B1 | 10/2002 | Ibsen et al. |
| 6,458,380 B1 * | 10/2002 | Leaderman ............... 424/443 |
| 6,471,947 B2 | 10/2002 | Bhakoo et al. |
| 6,475,472 B2 | 11/2002 | Joiner et al. |
| 6,479,037 B1 | 11/2002 | Montgomery |
| 6,485,709 B2 | 11/2002 | Banerjee et al. |
| 6,488,913 B2 | 12/2002 | Orlowski et al. |
| 6,488,914 B2 | 12/2002 | Montgomery |
| 6,500,408 B2 | 12/2002 | Chen |
| 6,503,485 B1 | 1/2003 | Allred |
| 6,503,486 B2 | 1/2003 | Xu et al. |
| 6,509,007 B2 | 1/2003 | Rajaiah et al. |
| 6,514,483 B2 | 2/2003 | Xu et al. |
| 6,514,484 B2 | 2/2003 | Rajaiah et al. |
| 6,517,350 B2 | 2/2003 | Diasti et al. |
| 6,682,721 B2 | 1/2004 | Kim et al. |
| 6,689,344 B2 | 2/2004 | Chang et al. |
| 6,730,316 B2 | 5/2004 | Chen |
| 6,780,401 B2 | 8/2004 | Kim et al. |
| 2002/0081555 A1 | 6/2002 | Weisel |
| 2003/0194382 A1 | 10/2003 | Chang et al. |
| 2004/0136927 A1 | 7/2004 | Kim et al. |
| 2005/0031554 A1 | 2/2005 | Kim et al. |

FOREIGN PATENT DOCUMENTS

| | | |
|---|---|---|
| JP | 10-17448 | 1/1998 |
| JP | 10-17448 A | 1/1998 |
| JP | 2000-281548 A | 10/2000 |
| WO | WO9517158 A1 | 6/1995 |
| WO | WO98/55044 A1 | 12/1998 |
| WO | WO 99/62472 * | 12/1999 |
| WO | WO9962472 A1 | 12/1999 |
| WO | WO0054699 A1 | 9/2000 |
| WO | WO0168045 A1 | 6/2002 |

OTHER PUBLICATIONS

Chalykh et al., Fracture Mechanics of Poly (N-vinyl Pyrrolidone) Poly (Ethylene Glycol) Hydrogel Adhesive Joints, Polym. Mater.Sci. Eng., vol. 81, 1999, pp. 427-428.

U.S. Appl. No. 10/915,283, filed Aug. 10, 2004 (and Preliminary Amendment) filed Aug. 10, 2004 entitled "Patches for Whitening Teeth"; 40 pp.

* cited by examiner

METHOD AND DEVICE FOR TEETH WHITENING USING A DRY TYPE ADHESIVE

RELATED APPLICATIONS

This application is a continuation-in-part of U.S. application Ser. No. 10/445,589 filed May 27, 2003, which is a continuation of U.S. application Ser. No. 10/049,817 filed Feb. 19, 2002, which is the national stage of PCT Application No. PCT/KR01/00207 filed Feb. 13, 2001. Each of these applications is incorporated herein by reference in its entirety for all purposes.

FIELD OF THE INVENTION

The present invention relates to a dry type patch for teeth whitening in which a peroxide as a tooth whitening agent is stabilized, and more particularly to a novel dry type patch for tooth whitening comprising a matrix type adhesive layer and a backing layer wherein the adhesive layer contains a peroxide as a teeth whitening agent and a hydrophilic glassy polymer as a base polymer so that the hydrophilic glassy polymer provides strong adhesion to teeth when being hydrated at the enamel layer of the teeth in the moist oral cavity and the whitening agent is released. In addition, since the dry type patch maintains excellent adhesion after being hydrated, it can be attached to the teeth for a long time and thus exhibits excellent whitening properties even at low concentrations of whitening agent. Furthermore, the dry type patch can provide excellent whitening properties within a short period of time.

BACKGROUND OF THE INVENTION

As people's interest in whitening their teeth increases, a number of tray products providing teeth whitening in a short period of time have become commercially available. A dentist-prescribed at-home bleaching product using a tray customized to fit a wearer is intended for overnight use for 2 weeks. However, since the wearer must keep his mouth closed while asleep for 2 weeks, the product is very inconvenient to use. For this reason, dentists have said that people prefer in-office bleaching products capable of providing whitening in only one dental treatment. In order to shorten the 2-week period to a single dental treatment, hydrogen peroxide at a concentration as high as 30~35% is used. In this case, an element such as a rubber dam must be used to prevent contact of the whitening product with body parts other than the teeth. As another technique, it is known that hydrogen peroxide at a concentration of about 16% can be combined with the use of laser, heat activator or photo activator to exert synergistic effects. The in-office bleaching product of this type has disadvantages of severe irritation and earlier retention due to the use of hydrogen peroxide at such a high concentration. In addition, although there has been considerable interest in in-office bleaching products and at-home bleaching products, these products are disadvantageous in that they are expensive and a wearer needs to regularly visit a dentist.

Accordingly, there is a need for over-the-counter (OTC) products for teeth whitening which exhibit whitening properties comparable to dental treatment without the aid of a dentist at low cost. A number of teeth whitening products using trays for OTC products are now available at low cost in supermarkets and drugstores, but are known to have many problems. For example, since the OTC products use one-sized and single-shaped trays, they do not fit various sizes and shapes of users' teeth, which causes irritation to the teeth due to poor fitting trays and gels excessively applied onto the trays. In addition, since the leakage of gel may take place in use, there are problems in terms of convenience and safety. Further, since most of the OTC products are highly noticeable, it is difficult to use them on a daily basis. Furthermore, the users of OTC products must keep their mouth closed for a long time during use.

In order to solve these problems of conventional teeth whitening products using trays, Japanese Patent Laid-open No. Hei 10-017,448, assigned to Lion Corp., discloses a plaster in a sheet form for the oral cavity which comprises a teeth adhesive layer and a supporting layer. Examples of whitening agents which can be used in the plaster include kojic acid and derivatives thereof, ascorbic acid and derivatives thereof, carbamide peroxide and the like. Among them, kojic acid and various salts thereof are particularly effective. However, since the above-mentioned whitening agents are strong acids, they may cause irritation of the oral cavity due to their low pH. Such agents provide substantial whitening at a high acidity. However, it is difficult to obtain a plaster with good whitening without causing any irritation.

U.S. Pat. No. 5,310,563 ("Curtis et al.") suggested a strip for teeth whitening which comprises a capsule obtained by encapsulating peroxide or various active ingredients in a putty-like material using a silicon polymer. The adhesion of the strip for teeth whitening to the teeth results from the elasticity of the putty such as rubber. However, meaningful attention is not given to the shape of the strip. The strip has a drawback that since the peroxide is encapsulated in the putty-like material, the whitening properties are relatively poor although the strip is attached to the teeth for the same time period. Further, since the adhesion between the strip and the teeth depends on the elastic strength, some stimuli such as coughing or collision with something in a mouth such as a tongue may separate the strip from the teeth.

On the other hand, U.S. Pat. No. 6,435,873 discloses a strip for teeth whitening using a gel retention insert without the use of a tray. The gel retention insert is a product that was developed in order to further enhance the adhesion between gel and the teeth, and has a microstructure. The gel retention insert has a microstructure in which a PSA (pressure sensitive adhesive) is used and teeth whitening ingredients are dispersed. However, the teeth whitening effects of the gel retention insert are not verified. Since typically polymers used as PSAs employ solvents unsuitable for oral products, e.g., methylene chloride or ethylacetate, etc, instead of water or alcohol, they are considered to be unsuitable to directly attach to the teeth in the oral cavity. In addition, in the case of an acrylic polymer (a wet PSA) which has a low compatibility with a peroxide, the resulting strip for teeth whitening is thought to be inappropriate for commercialization.

U.S. Pat. No. 6,419,906, issued to Colgate, discloses a strip for teeth whitening comprising a thermoplastic ethylene oxide polymer and a solid percarbonate as a teeth whitening agent. However, since the ethylene oxide polymer has poor adhesion to the teeth, it is believed that the wearability of the strip is poor.

In particular, teeth whitening strips were commercialized by P&G. The teeth whitening strip is manufactured by uniformly and thinly coating teeth whitening ingredients onto a thin and flexible polyethylene strip without the use of a tray and, thus, problems of conventional tray products can be avoided. However, since the teeth whitening strip is a wet type strip, the adhesive strength of the strip to the teeth is not so strong. Accordingly, the strip can be easily attached and peeled off, but has a drawback in that when coughing and laughing out loud, it does not remain attached at a desired position for a desired period of time and can be easily detached from teeth. Since the strip for teeth whitening has poor adhesion to the teeth, a wearer may also feel an unnatural sensation. In addition, since the teeth whitening strip is not closely fixed to the teeth, a wearer feels that the strip is loose and cannot continuously wear the strip for 30 minutes or more. According to one study from P&G, the concentration of hydrogen peroxide as a whitening agent contained in the wet type product sharply decreases 30 minutes after adhesion, and thereafter does not contribute to whitening effects. A recently published U.S. patent application Ser. No. 2003/0219389 discloses tooth whitening products. According to this patent application publication, the concentration of a whitening agent in a tooth whitening substance is a main factor among many factors capable of enhancing whitening effects. The patent publication also mentions that hydrogen peroxide having a concentration of 7.5% or more and a density of about 1.3 mg/cm$^2$ or less in a tooth whitening composition causes a tolerable degree of irritation. However, the degree of irritation is dependent on individuals. In addition, since it is well known that high concentration hydrogen peroxide involves severe irritation, improvement in whitening properties using low concentration hydrogen peroxide is preferred. In particular, when the wet type products from P&G are touched by the hands or contact the skin, the whitening agent begins to be released since the wet type gel is already hydrated. As a result, discoloration of the hands or skin occurs even by a product containing 5.3% hydrogen peroxide.

In conclusion, since high concentration hydrogen peroxide involves severe irritation, it is desirable to provide products and methods that improve teeth whitening, convenience in use, and safety without increasing the concentration of hydrogen peroxide.

SUMMARY OF THE INVENTION

A dry type adhesive device for teeth whitening in which a peroxide tooth whitening agent is stabilized is disclosed. The dry type adhesive device for tooth whitening comprises a matrix type adhesive layer and a backing layer wherein the adhesive layer contains a peroxide as a teeth whitening agent and a hydrophilic glassy polymer as a base polymer so that the hydrophilic glassy polymer provides strong adhesion to teeth when hydrated at the enamel layer of the teeth in the moist oral cavity and the whitening agent is released. In particular, although the dry type adhesive device is touched with the hands or contact the skin during attaching to the teeth prior to hydration, no stickiness and releasing of the whitening agent takes place, thus being safe. In addition, since the dry type patch has strong adhesive strength to the teeth and excellent adhesion maintenance after being hydrated and attached to the teeth, it can remain attached to the teeth for a long time and thus exhibits excellent whitening effect even low concentrations of a whitening agent. Furthermore, the dry type adhesive device can provide excellent whitening within a short period of time.

The present invention comprises a dry type adhesive device for tooth attachment. The device comprises a matrix type adhesive layer and a backing layer. The adhesive layer contains a peroxide teeth whitening agent and a hydrophilic glassy polymer as a base polymer so that the hydrophilic glassy polymer provides strong adhesion to teeth when hydrated and contacted with teeth and little or no adhesion prior to hydration. The adhesive strength is maintained substantially constant while the teeth whitening agent is released from the adhesive layer. Effective teeth whitening is achieved by using an adhesive layer having minimum depth requirements depending upon the peroxide concentration.

DETAILED DESCRIPTION OF THE INVENTION

It is generally known in the art that factors influencing teeth whitening include the concentration of peroxide as a whitening agent, contact time between a whitening agent and teeth, usage frequency of a whitening agent, pH, temperature, surface debridement of the tooth surface, sealed environment and the like.

The fact that high concentration peroxide improves whitening effects is better explained by the teeth whitening mechanism. Teeth have many small holes which are invisible to the naked eye. These holes are formed in not only the outermost enamel layer of the teeth, but also the inner dentin layer. Coloring ingredients permeate into the enamel layer and the dentin layer through the holes, and turn the teeth yellow. According to the teeth whitening mechanism, peroxide having a low molecular weight can permeate into the holes formed in the enamel and dentin layers, and acts as a strong oxidizing agent to bleach the coloring ingredients. This bleaching cleaves bonds expressing colors of the coloring ingredients and thus whitens the teeth. Since the bleaching is a diffusion reaction, high concentration peroxide rapidly permeates into the teeth. Accordingly, high concentration is very effective in whitening the teeth. However, peroxide can permeate into gums, as well as the teeth, causing irritation to the gums, and may further permeate into the innermost nerve layer. In this case, since the peroxide may cause transient tooth sensitivity, it causes unwanted adverse side effects. Accordingly, although high concentration peroxide is the most effective at providing whitening within a short period of time, there is a limitation in terms of safety.

The contact time between a whitening agent and the teeth is associated with the tooth whitening mechanism in which the diffusion of peroxide provides whitening. That is, since a long contact time between peroxide and teeth facilitates the permeation of the peroxide into the enamel layer of the teeth, it is a method effective for providing whitening effects within a short period of time. However, a product, e.g., a tray, causing an unnatural sensation, being highly noticeable upon wearing and inconvenient to while talking causes inconvenience in the wearer's daily life. Since high adhesive strength and maintenance of tooth adhesion are required to provide adhesion for a sufficient period of time, a strip product in which a gel is thinly coated, such as a wet type product, is unsuitable.

Usage frequency is also associated with peroxide concentration and contact time. Although peroxide is stable when it is initially applied to the teeth, it begins to be decomposed due to its high reactivity over time after the peroxide is contacted with discolored teeth in the oral cavity. Accordingly, separate use of a peroxide several times is advantageous over continuous use of the peroxide (e.g., for 3 hours), in terms of whitening effect. However, excessively frequent use causes the wearer inconvenience. Appropriate control over the usage frequency of peroxide is required.

pH is a factor in the formation of highly reactive radicals in a peroxide. Temperature is a factor increasing the reaction rate of the whitening reaction by the peroxide. However, care should be taken not to cause irritation due to too high pH and temperature.

Surface debridement and sealed environment can be achieved with ease so long as the adhesion to teeth is excellent. These conditions are seldom achieved by tray type and wet type products. In contrast, the use of dry type products containing a hydrophilic glassy polymer with excellent adhesion to teeth can provide the surface debridement and sealed environment.

The present inventors have earnestly and intensively conducted research to develop a product which can be safely and conveniently used while effectively improving whitening effects. To this end, the present inventors have found that the concentration of a whitening agent is an important factor for improved whitening effects when a constant attachment time is used (e.g., 30 minutes at a time). However, the present inventors conducted experiments to evaluate whitening effects without limiting the contact time. As a result, the present inventors found that the most important factor is achieving a one-contact time that provides the desired amount of whitening effect.

Under the same concentration of peroxide, the longer the contact time is, the better the whitening effects. However, prior art tray products have problems in that the tray causes physical irritation, and a gel flows into the oral cavity due to biting the gel-applied tray with teeth for a long period of time. Wet type patch products,. e.g., Crest Whitestrips (P&G), in which a peroxide gel is thinly coated on a polyethylene (PE) strip, have difficulty in attachment for 30 minutes or more due to their poor adhesiveness strength. The present inventors have found that a dry type patch containing a hydrophilic glassy polymer in an adhesive layer can be firmly attached to teeth and can maintain strong adhesion despite the passage of time. The present invention is based on these findings. Therefore, it is an object of the present invention to provide a dry type patch which exhibits excellent whitening effects with the use of a whitening agent at a low concentration by ensuring a sufficient one-contact time.

In order to obtain a sufficient one-contact time, the thickness of adhesive layer has to be controlled. If the thickness of adhesive layer is too thin, it is hard to obtain the strong adhesive strength for an extended period of time. So, it is preferred to adjust the minimum thickness of adhesive layer according to the desired one-contact time. For example, in the case of low concentrations of peroxide such as 3%, the minimum desirable one-contact time is at least 60 minutes, and the minimum thickness of adhesive layer is at least about 100 μm. At low peroxide concentrations, the preferred one-contact time is more than 90 minutes, and the preferred thickness of adhesive layer is more than 150 μm. The more preferred one-contact time is 120 minutes or more, and the more preferred thickness of adhesive layer is at least 200 μm in case of low concentration of peroxide in the range of 1% to 4%.

In the case of medium peroxide concentration of between 4% and 7.5%, the proper minimum one-contact time and thickness of adhesive layer are changed. In that case, the minimum desirable one-contact time is at least 30 minutes, and the minimum thickness of adhesive layer is at least 60 μm. The preferred one-contact time is at least 60 minutes, and the preferred thickness of adhesive layer is 80 μm or greater.

In case of high peroxide concentration of more than 7.5%, the desirable minimum one-contact time and thickness of adhesive layer are changed. In that case, the minimum one-contact time is at least 15 minutes, and the minimum thickness of adhesive layer is preferably 40 μm or greater. The preferred one-contact time is at least 30 minutes, and the preferred thickness of adhesive layer is 50 μm or greater.

In this invention, it has been found that the thickness of adhesive layer is an important factor in achieving the desired one-contact time and whitening effect. Adhesive layer thickness is believed to be more important than concentration of whitening agent as like peroxide. The thicker the thickness of adhesive layer, the whitening efficacy is increased.

In order to achieve the object of the present invention, there is provided a device for tooth attachment comprising a dry matrix type adhesive layer and a backing, wherein the adhesive layer contains a peroxide as a teeth whitening agent and a hydrophilic glassy polymer as a base polymer so that the hydrophilic glassy polymer provides strong adhesion to teeth while being contacted with teeth, the whitening agent begins to be released and the adhesive strength is maintained relatively constant, thereby being convenient to use during a long one-contact time and exhibiting excellent whitening effects at low peroxide concentrations.

In the present invention, the whitening effects are determined according to the change in color before and after use of the product. The change in color is evaluated using a shade guide or chromameter. The former is carried out by measuring a level of the shade guide to which a color before use of the product corresponds, and measuring a level of the shade guide to which a color after use of the product corresponds. The latter is carried out by measuring a Lab (L) value. The L value represents brightness. 0 indicates black, and 100 indicates white. In the present invention, the ΔL value was determined as a value indicating whitening effects of the product. Since the evaluation using a shade guide is carried out after using the product for a predetermined time, it is difficult to test numerous formulations or examples, which is disadvantageous in terms of time and cost. In the present invention, the whitening effects were evaluated by measuring Lab values of artificial teeth using a chromameter.

In order to manufacture the dry type device of the present invention, the hydrophilic glassy polymer is used as a main polymer of the adhesive layer. The hydrophilic glassy polymer provides strong adhesion to teeth and releases a teeth whitening agent after being hydrated at the enamel layer of the teeth in the moist oral cavity.

A patch for teeth whitening using no tray (e.g. non-tray type) exhibits excellent teeth whitening effect only by attaching the patch to teeth. However, when the patch includes a wet adhesive layer, and particularly is gel-type, it may leave a considerable amount (80% or more) of active material or adhesive material on hands upon peeling off the patch from a release liner. Further, when the patch is contacted with user's face or lips due to the user's mistake, adhesive material contained in the adhesive layer remains on the face or lips. Moreover, undesired results may be obtained depending on the kind or content of the teeth whitening agent. Particularly, when a high concentration peroxide having a strong bleaching effect is used as a teeth whitening agent, serious problems may occur. On the contrary, active material and adhesive material contained in the dry type patch of the present invention are maintained in the state of a solid (sheet or film) before hydration. When the patch contacts with the skin or is detached from the teeth, only small amounts on the order of about 0% to 10% of the active material and adhesive material are left. Accordingly, the dry type patch of the present invention is proved to be safe and convenient to use.

Non-tray patches or trays for teeth whitening are required to show excellent adhesive strength comparable to physical properties of mucoadhesives, e.g., AFTACH (Distributor: Dong-Wha Pharm. Ind. Co., Ltd., Korea, Manufacturer: TEIJIN, Japan) and Taisho-A (Distributor: Taisho Pharmaceutical Co., Ltd., Japan, Manufacturer: TEIYAKU, Japan), used for treating stomatitis. That is, they must have adhesive strength sufficient to exhibit desired effects in the moist oral cavity for a desired period of time. In addition, they are required to have adhesive strength so as not to be detached from the teeth even in unexpected situations, e.g., sudden coughing and shouting in a loud voice. Furthermore, it is preferred that the non-tray patches or trays for teeth whitening have low adhesive strength prior to attachment to the teeth. This is because too strong an initial adhesive strength may cause problems upon detaching from a release liner by hand. The dry type patch or appliance of the present invention may easily solve such problems. The dry type patch or appliance of the present invention has very low adhesive strength before the adhesive layer of the patch or appliance is hydrated. The dry type device provides strong adhesive strength after hydration (see, Table 3). Even when the dry type device is completely hydrated, it can be easily detached by hand. If the adhesion to the teeth is too strong, drinking of a quantity of water (mouthwash, brushing, drinking water or beverage) facilitates the detachment from teeth. Accordingly, the dry type device of the present invention is advantageous in terms of convenience in use.

The backing may consist of layer containing a water-insoluble and water-impermeable polymer as a film formed in order to prevent the patch from sticking to the gums or tongue and from deforming or being detached from the teeth by saliva. Alternatively, the backing may be other materials such as a deformable layer of wax, plastic or fabric.

On the other hand, there may be a problem that peroxide used as a teeth whitening agent in the dry type device for teeth whitening becomes unstable as time goes by. In order to solve the instability of peroxide in the present invention, a peroxide stabilizer may be used, or a solution of a glassy polymer having a good compatibility with peroxide is added by adjusting the solvent ratio without using peroxide stabilizer. Thus, the present invention provides a new type device in which a hydrophilic glassy polymer is used as a base polymer for an adhesive layer of a dry type using a peroxide as a teeth whitening agent, and a peroxide stabilizer or a solution of a glassy polymer having a good compatibility with the peroxide is added by adjusting the solvent ratio, instead of the peroxide stabilizer. The new type device of the present invention can ensure the stability of peroxide.

In order to enhance the whitening effect of the device for teeth whitening according to the present invention, a polyphosphate may be used together with peroxide as a teeth whitening agent.

The teeth whitening effect of the teeth whitening device according to the present invention may be controlled by varying the kind and concentration of the whitening agent. In addition, since the patch for teeth whitening according to the present invention has good adhesion to teeth, and begins to be hydrated and becomes transparent upon wearing, no marks are noticeable during wearing and thus the wearer's daily life is not affected. In addition, since the wearer can observe oxygen bubbles generated by peroxide upon wearing, the wearer can visually recognize the whitening effects.

Generally, most people recognize their tooth discoloration and consider the necessity of teeth whitening in their teens. Since the tooth discoloration has been ongoing for the past decades, a certain period of usage of teeth whitening products is necessary to return to the teeth to their initial state. For this reason, it is required to steadily use tooth whitening products for each use period over an extended period of time, e.g., 1 or 2 weeks. In order to motivate steady use, the teeth whitening products must have less irritation, be convenient to use without disturbing the wearer's daily life, and provide whitening effects within a short period of time.

The present inventors have found that the dry type adhesive device of the present invention can improve the whitening effects within a short period of time. Increased usage frequency is the most effective method in exhibiting whitening effects within a short period of time. However, excessively frequent use of a teeth whitening product may cause the wearer inconvenience in use and involve irritation. In addition, when the usage frequency is limited to once or twice, it takes a relatively long time, e.g., 1 to 2 weeks or longer and thus the wearer tends to feel inconvenienced. An alternative method is carried out by increasing the concentration of the whitening agent. However, this method unfavorably involves irritation to the teeth, and may discolor hands, skin, gums, mucous membranes and tongue upon contacting them with the whitening agent.

Thus, the present inventors have developed a method for improving whitening effects without increasing the concentration of the whitening agent and usage frequency. As a result, the present inventors have found that strong adhesiveness and adhesion maintenance after hydration of the dry type adhesive device provide the wearer with convenience in use and ensure sufficient one-contact time. The present inventors have also found that the contact time and adhesive layer thickness are more important factors in improvement of whitening effect than adhesion frequency or the concentration of whitening agent. The present invention is based on these findings.

In order to obtain the improved whitening effects, this invention suggests that "teeth whitening set" comprised of two products one for Day-Time-Use and the other for Night-Time-Use. Generally it is hard to avoid drinking and eating more than 60 minutes in Day-Time because there are too many activities in Day-Time. So, it is suggested the product which has relative short one-contact time and relative high concentration of peroxide is proper to Day-Time-Use.

In case of Day-Time product, the minimum peroxide concentration is at least 6%, preferred at least 9%, and more preferred at least 10%. And the minimum one-contact time is less than 15 minutes, preferred less than 30 minutes, and more preferred less than 60 minutes. The minimum thickness of adhesive layer is at least 40 μm, preferred at least 50 μm, and more preferred at least 60 μm.

On the other hand, it is possible that the formulation for Night-Time-Use is designed to have relative long one-contact time because there is much more uninterrupted time available than in Day-Time. At night, because people feel tired, a higher the concentration of peroxide can be more sensitive on teeth and soft oral tissues. So, a lower concentration and longer one-contact times is better for the Night-Time-Use. In Night-Time, it is possible to attach the tooth whitening product for more than 2 hours if it is comfortable and convenient for use.

In case of Night-Time product, the maximum concentration is about 10% or less, preferably about 9% or less, and more preferably about 6% or less. And the minimum one-contact time is at least 60 minutes, preferred at least 90 minutes, and more preferred at least 120 minutes. And the minimum thickness of adhesive layer is 80 μm or greater, preferred 100 μm or greater, and more preferred 120 μm or greater.

Since the dry type adhesive device for teeth whitening of the present invention essentially contains a hydrophilic glassy polymer as a main ingredient of the adhesive layer, it exhibits strong adhesive strength after hydration and maintains a constant stickiness level during adhesion. In addition, since whitening effects can be maximized when one-contact time is lengthened and the concentration of the whitening agent is maintained above a particular level, it is preferred that the peroxide contained in the dry type patch is stabilized. To better stabilize the whitening agent, particularly, peroxide, contained in the formulation, a peroxide stabilizer is used in the present invention. It is to be understood that if the formulation contains a polymer which is highly compatible with the peroxide, the peroxide stabilizer is not an essential ingredient.

The longer the one-contact time, the better the whitening effect. In particular, it has been found that as the contact time is lengthened, the whitening effect on densely discolored canine teeth is excellent. Accordingly, overnight use of the device according to the present invention is recommendable in terms of whitening effect. Although the dry type adhesive device of the present invention is intended for overnight use, it is convenient to use and causes no physical irritation because it uses no tray. In addition, the dry type adhesive patch of the present invention does not have many inconveniences, such as a gel flowing into the throat. These advantages of the dry type adhesive device of the present invention are due to strong adhesive strength and adhesion maintenance.

However, since overnight use of the dry type adhesive device may prevent sensitive persons from sleeping, the device is generally used when awake.

Meanwhile, the use of the whitening agent at a low concentration for too short a time cannot achieve satisfactory whitening effects. One-contact time is commonly 30 minutes or more, more preferably 1 hour or more, and most preferably 2 hours or more.

The present inventors evaluated the whitening effects of the dry type patch under various usage frequencies for the same one-contact time (30 minutes). As a result, the present inventors have found that a signficant factor influencing the whitening effects is the concentration of the whitening agent, i.e. peroxide (see, Table 2 below). A dry type adhesive patch containing 9% hydrogen peroxide exhibited better whitening effects than a wet type patch containing 9% of hydrogen peroxide both for a one-contact time of 30 minutes. In particular, a dry type adhesive patch containing 3% hydrogen peroxide for a one-contact time of 2 hours exhibited better whitening effects than a wet type patch containing 14% hydrogen peroxide and a dry type adhesive patch containing 9% hydrogen peroxide both for a one-contact time of 30 minutes (see, Table 2 below).

The patch for teeth whitening of the present invention is a matrix type patch, and is intended to be attached not to skin or mucous membrane but to the enamel layer of the teeth so as to supply a teeth whitening agent to the surface of teeth for a sufficient time to whiten the teeth. In the present invention, a hydrophilic glassy polymer is used as a material for various layers of the matrix type patch. By this patch structure, the release of a whitening agent is prevented when storing and attaching the patch to teeth using hands. After the patch is attached, the patch begins to be hydrated by moisture on the tooth surface and thus adhesive strength is obtained so that the whitening agent is released. A hydrophilic glassy polymer is used as a material for various layers of the matrix type patch. Therefore, in accordance with another aspect of the present invention, a hydrophilic glassy polymer is used as a material for layers of the matrix type patch other than the backing layer.

For these purposes, examples of the glassy polymer which can be used in the adhesive layer of the patch according to the present invention include polyalkylvinyl ether-maleic acid copolymer (PVM/MA copolymer, Gantrez AN 119, AN 139 and S-97), polyvinyl alcohol, polyacrylic acid, Poloxamer 407 (Pluronic), polyvinyl pyrrolidone-vinyl acetate copolymer (PVP/VA copolymer; Luviskol VA and Plasdone S PVP/VA), polyvinyl pyrrolidone (PVP, K-15~K-120), Polyquaternium-11 (Gafquat 755N), Polyquaternium-39 (Merquat plus 3330), Carbomer (Carbopol), hydroxypropylmethyl cellulose, hydroxyethyl cellulose, hydroxypropyl cellulose, gelatin and alginate salt such as sodium alginate. The above-described polymers can be used alone or in mixtures thereof. Solvents for these polymers include water, ethanol or mixtures thereof with varied mixing ratios.

The patch to be attached onto teeth should be flexible enough to be deformable so that it conforms to contours of teeth. Since some polymers have poor flexibility, suitable plasticizers may be added. The plasticizer is dependent on the kind and preparation of the glassy polymer, but polypropylene glycol, glycerin or polyethylene glycol is generally used as the plasticizer.

The teeth whitening agent contained in the tooth enamel adhesive layer may be selected from the group consisting of hydrogen peroxide, carbamide peroxide, calcium peroxide, sodium percarbonate, sodium perborate, tetrasodium pyrophosphate peroxidate and mixtures thereof. Tetrasodium pyrophosphate peroxidate (TSPP-$H_2O_2$), which is an addition compound of tetrasodium pyrophosphate and hydrogen peroxide, displays properties of tetrasodium pyrophosphate, per se, as well as properties of hydrogen peroxide in a state of an aqueous solution or crystal. Usually, tetrasodium pyrophosphate stabilizes hydrogen peroxide without changing intrinsic properties of hydrogen peroxide. In other words, it prevents the problems caused by using hydrogen peroxide alone. Decomposition of hydrogen peroxide may be promoted by metallic catalase, UV-ray, oxidase, thermal treatment, etc., whereas tetrasodium pyrophosphate peroxidate is stable against the above-described materials and treatments and displays intrinsic properties and functions of hydrogen peroxide. In practice, using tetrasodium pyrophosphate peroxidate in a liquid, gel or paste phase shows good stability with time at a temperature of 40° C., as compared to using peroxide alone. However, even though using tetrasodium pyrophosphate peroxidate, the stability of peroxide in the patch cannot easily achieved.

In general, peroxide is known to be difficultly stabilized in a patch product due to its high reactivity. Further, it has poor compatibility with polymers. The stability of peroxide in products relates to a type or preparation of the products. In connection with the stability of peroxide in products, there are many patents dealing with the stabilization of peroxide in ordinary gel, paste or solution phase and some of them are found to assure stability to some extent at a high temperature. However, there is no suggestion with respect to the stabilization of peroxide in a thin-coated adhesive or patch. The present inventors likewise found after conducting many studies that such problem cannot necessarily be solved by means of known peroxide stabilizers.

Now, the inventors have discovered a stabilizer, which can be used within range in application of the present invention without harming fundamental properties of the patch according to the present invention and can improve the stability with time of peroxide in the patch at a high temperature Therefore, in accordance with another aspect of the present invention, a peroxide stabilizer is used together with peroxide as a teeth whitening agent.

The peroxide stabilizer having a good compatibility with the peroxide which can be used in the patch for teeth whitening of the present invention is one or more selected from the group consisting of alkylaryl sulphonates, alkyl sulphonates, alkyl carboxylates, alkyldiphenyloxide disulphonates, a series of Span such as Span 20 (sorbitan monolaurate), Span 40 (sorbitan monopalmitate), Span 60 (sorbitan monostearate), Span 80 (sorbitan monooleate) and Span 85 (sorbitan trioleate), TWEEN (POE sorbitan fatty acid ester) series. More detailed explanation for the peroxide stabilizer is explained below.

The patch for teeth whitening according to the present invention contains peroxide as a main teeth whitening agent. When the patch is manufactured using the teeth whitening agent only and then stored in 40° C., the content of the peroxide in the patch decreases as time goes by. Accordingly, the whitening effect of the patch in vitro are also observed to be lower, compared to a new patch. For a gel type formulation, loss of peroxide with time is small even when excessive polymer is used as a film former and a peroxide stabilizer is not added. Even when the preparation has low peroxide stability, the desired effect can be obtained by using a small amount of a chelating agent, such as EDTA or sodium citrate, known as a common peroxide stabilizer. In a teeth whitening patch wherein the solvent of the adhesive layer is evaporated to form a sheet-shaped patch, when a stabilizer is not used in the preparation, the peroxide stability is diminished compared to the gel type formulation. It is also observed that the addition of a chelating agent results in a decrease in the peroxide stability of the dry type adhesive patch, compared to a patch without a chelating agent. Furthermore, even when using Dequest phosphonates, which are known for their superior peroxide stabilizing effects, suitable peroxide stabilization cannot be obtained.

As described above, the reason why the peroxide stability in the patch differs in accordance with the type of formulations such as gel, liquid or sheet maybe explained in a variety of ways. According to U.S. Pat. No. 4,320,102, peroxide is described as being readily decomposed through a reaction catalyzed by a minimal amount of metal contained in the composition. There have been reported data showing that the presence of 0.1 mg of iron, 0.2 mg of copper, 0.1 mg of magnesium or 0.02 mg of chromium per one liter of a peroxide will lead to decomposition of the peroxide. A sheet-type patch formed by evaporation of the solvent in a solution-type patch would include a high content of metal on the thin sheet of patch. Further, a sheet-type patch has a large surface area, which allows a high rate of reaction on the surface, and also lowers the stability of the peroxide. The stabilizer contained in the patch according to the present invention is mostly a surfactant or emulsifier, which is believed to form micelles and produce preferable effects on the peroxide stabilization of the product. For example, the stabilizer prevents the contact between the peroxide and material having low compatibility with the peroxide, uniformly disperses a whitening agent in the patch when a glassy polymer having poor spread-ability is used, and allows an adhesive layer to be uniformly cast or applied to a backing. In practice, it was found that when gel is applied coated over a large surface area, the residual amount of peroxide decreases with time, while a gel of the same composition, contained in a container, is stable at a relatively high temperature. The present inventors found that since some hydrophilic glassy polymers have a good compatibility with peroxide, a solution of the hydrophilic glassy polymer with adjusted solvent ratio can sufficiently stabilize the peroxide without the use of a peroxide stabilizer. Accordingly, the present invention is not limited to a combination of peroxide and a peroxide stabilizer. Now, more detailed description is described below.

Hydrophilic glassy polymers such as polyvinyl pyrrolidone (PVP, K-15~K-120), Polyquaternium-11, Polyquaternium-39, polyvinyl pyrrolidone-vinyl acetate copolymer (PVP/VA copolymer) are highly compatible with peroxides and are easily soluble in water, ethanol or a mixture thereof. Accordingly, peroxide in the patch can be stabilized by using a mixture of water and ethanol in a mixing ratio of 9:1 to 0:10, without using a peroxide stabilizer. It is believed that the good compatibility of polyvinyl pyrrolidone with a peroxide results from the stabilization of peroxide by formation of a complex with polyvinyl pyrrolidone via hydrogen bonding. Polyvinyl pyrrolidone (PVP) is the most preferred hydrophilic glassy polymer to be used in the active ingredient-containing layer containing peroxide. Among the available PVP, K-15~K-120 are used, and K-90 (PVP) is preferably used in the patch of the present invention. K-30 (PVP) is more preferable since higher solid content is desired in the efficiency upon producing by a casting method. Preferably, the PVP has a relatively high molecular weight, preferably greater than about 500,000, and more preferably greater than about 1,000,000. In a preferred embodiment, PVP having a molecular weight of 1,270,000 is used. Further, peroxides are found to be highly compatible with polymers having quaternary ammonium structure, such as polyquaternium. According to the present invention, a mixture of water and ethanol is used as solvent for adhesive materials. Glassy polymers which are highly compatible with peroxide are typically so hydrophilic that they cannot be uniformly coated on the surface of a release liner or other sheet. The mixture of water and ethanol can solve such problem so as to form a uniform sheet layer. Therefore, in accordance with another aspect of the present invention, there is provided a patch for tooth whitening comprising peroxide as a tooth whitening agent and a glassy polymer having a good compatibility with the peroxide, wherein the peroxide is stabilized at a high temperature by adjusting the ratio of water and ethanol without addition of a peroxide stabilizer. Also, the patch of the present invention further comprises a plasticizer to provide a sufficient flexibility for the patch. Suitable plasticizers include propylene glycol, glycerin, and polyethylene glycol although it will vary depending on the kind and preparation of the polymer used.

Further, the present invention may include a polyphosphate as a whitening aid agent other than peroxide as a main whitening agent in order to enhance whitening effects. Polyphosphates which can be used in the present invention include one or more selected from the group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), acidic sodium metapolyphosphate (Sporix) and acidic sodium polyphosphate (Multiphos). In general, it is known that polyphosphate may be used effectively as a tartar controller in toothpaste to inhibit the formation of dental calculus or to remove dental calculus. Polyphosphate is also known as a good chelating agent to enhance the teeth whitening effects to some extent since it can effectively remove stains formed on the surface of the teeth, especially those formed of metal such as iron, calcium, magnesium, etc. derived from foods or working circumstances. It has been found that polyphosphate used along with peroxide in the patch according to the present invention may inhibit scale formation and remove dental calculus by lengthening the contact time between the teeth and the polyphosphate. In practice, it is observed that when attaching the patch of the present invention to the teeth, the surface of teeth and gaps between teeth get cleaned.

Polymers which can be used in the backing layer of the matrix type patch according to the present invention include polyvinyl acetate, ethyl cellulose, polymethyl methacrylate, methacrylic acid copolymers, e.g., methacryloylethyl betain/methacrylate copolymer (Yukaformer, manufactured by Mitsubishi), methacrylic acid copolymers (Eudragit L 100, Eudragit L 125, Eudragit L 100-55, Eudragit L 30D-55), aminoalkylmethacrylate copolymers (Eudragit E 100, Eudragit E 125, Eudragit RL 100, Eudragit RL 30D), cellulose acetate phthalate, Shellac and mixtures thereof. In addition, polymers used as enteric coating materials, which are not dissolved at pH 6 to 8 in the oral cavity, may be used.

The backing layer of the patch for teeth whitening according to the present invention may contain various plasticizers for sufficient flexibility. In this case, many kinds of plasticizer including the plasticizers described above, such as propylene glycol, glycerin, polyethylene glycol, can be used depending on the kind of the solvent used. For example, castor oil or hydrogenated castor oil may also be used.

Further, upon attaching the patch of the present invention to the teeth, in order to make the teeth visually white due to physical and chemical reactions, any white pigment may be used in the backing layer. For example, titanium dioxide, talc, hydroxyapatite, zinc oxide, or a mixture thereof may be used as the white pigment. When these pigments are not compatible with peroxide used as a whitening agent, surface-treated titanium dioxide may be used. In addition, it is possible to employ pearl material or pigments of a variety of colors depending on individual tastes.

In accordance with the present invention, substances such as enzymes, particularly dextranase or glucose oxidase, which cannot be used in conventional toothpaste due to their instability over time, may be used alone or in a mixture. It is also possible to add papain, which is known to have teeth whitening effects. For the treatment of oral diseases, triclosan, chlorhexidin, vitamin E or its derivatives such as vitamin E acetate, oxidants effective for treating halitosis, chlorophyll or its derivatives, flavors, etc., can be used.

DESCRIPTION OF THE PREFERRED EMBODIMENTS

Hereinafter, the present invention will be described in more detail with reference to the following examples. However, these examples are given for the purpose of illustration and are not to be construed as limiting the scope of the invention.

EXAMPLES 1 TO 5 AND COMPARATIVE EXAMPLES 1 TO 4

In accordance with the compositions described below, patches for teeth whitening of Examples 1 to 5 and Comparative Examples 1 to 4 were prepared. The layers are prepared using conventional extrusion or solvent casting processes. Each solution as indicated below is prepared and coated onto a suitable carrier substrate or casting drum to prepare layers by solvent casting. The solution is dried to form a film or layer.

Example 1

—Solution for Preparing Active Material-Containing Adhesive Layer

10% of polyvinyl alcohol, 10% of polyvinyl pyrrolidone, 1.5% of hydrogen peroxide, 1% of SAPP, 3% of glycerin, 1% of SLS and the balance of water —Solution for Preparing Backing Layer 8% of ethyl cellulose, 5% of Eudragit, 4% of castor oil and the balance of ethanol.

* Both casting process and extrusion process were possible. When manufactured by casting process, the concentration of hydrogen peroxide in the adhesive layer of the dry type patch was 3%. One-contact time was 120 minutes.

Example 2

—Solution for Preparing Active Material-Containing Adhesive Layer

20% of polyvinyl pyrrolidone, 4.5% of hydrogen peroxide, 10% of glycerin, and the balance of water —Solution for Preparing Backing Layer 5% of polyvinyl acetate, 5% of glycerin and the balance of ethanol.

* Both casting process and extrusion process were possible. When manufactured by casting process, the concentration of hydrogen peroxide in the adhesive layer of the dry type patch was 9%. One-contact time was 30 minutes.

Example 3

—Solution for Preparing Active Material-Containing Adhesive Layer

10% of Polyquaternium-39, 13% of carbamide peroxide, 5% of ethanol and the balance of water —Solution for Preparing Backing Layer 15% of Eudragit, 5% of propylene glycol and the balance of ethanol.

* Both casting process and extrusion process were possible. When manufactured by casting process, the concentration of the hydrogen peroxide in the adhesive layer of the dry type patch was 9% as carbamide peroxide was expressed by hydrogen peroxide. One-contact time was 30 minutes.

Example 4

—Solution for Preparing Active Material-Containing Adhesive Layer

12% of a copolymer of polyalkyl vinyl ether/maleic acid (Gantrez S-97), 15% of tetrasodium pyrophosphate, 0.5% of Sorbitan Oleate and the balance of water —Solution for Preparing Backing Layer 10% of ethyl cellulose, 6% of castor oil and the balance of ethanol.

* Both casting process and extrusion process were possible. When manufactured by casting process, the concentration of the hydrogen peroxide in the adhesive layer of the dry type patch was 9% as tetrasodium pyrophosphate was expressed by hydrogen peroxide. One-contact time was 30 minutes.

Example 5

—Solution for Preparing Active Material-Containing Adhesive Layer

20% of Polyquaternium-11, 5% of calcium peroxide, 4% of TKPP, 2% of Sorbitan monolaurate and the balance of water —Solution for Preparing Backing Layer 20% of ethyl cellulose, 5% of Eudragit, 12% of castor oil, 0.2% of Mint flavor and the balance of ethanol.

* Both casting process and extrusion process were possible. When manufactured by casting process, the concentration of the hydrogen peroxide in the adhesive layer of the dry type patch was 3% as calcium peroxide was expressed by hydrogen peroxide. One-contact time was 30 minutes.

Comparative Example 1

Crest Whitestrips Regular (P&G) (the concentration of the hydrogen peroxide in the adhesive layer was 6%)
One-contact time was 30 minutes.

Comparative Example 2

Rembrandt Quick White (the concentration of the hydrogen peroxide in the adhesive layer was 6%)
The product was manufactured by directly coating a gel containing hydrogen peroxide on a one-sized tray.
One-contact time was 15 minutes.

Comparative Example 3

Crest Whitestrips Professional Supreme (P&G) (the concentration of the hydrogen peroxide in the adhesive layer was 14%)
One-contact time was 30 minutes according to the manufacturer's protocol.

Comparative Example 4

—Solution for Preparing Active Material-Containing Adhesive Layer (Thickness: 400 μm)
10% of polyvinyl alcohol, 3.1% of propylene glycol, 0.5% of kojic acid, a small amount of methyl papaoxybenzoic acid and the balance of water
—Solution for Preparing Backing Layer
10% of ethyl cellulose, 4% of castor oil and the balance of ethanol.
One-contact time was not particularly set because the product was not yet commercially available.
Abbreviations used above have the following meaning:
TKPP: tetrapotassium pyrophosphate, SAPP: sodium acid pyrophosphate, TSPP; tetrasodium pyrophospha

Experimental Example 1

<Convenience in Use>

The patches for teeth whitening of Examples 1 to 5 were dry type adhesive patches, the product of Comparative Example 1 was Crest Whitestrip commercially available from P&G, U.S.A, the product of Comparative Example 2 was a one-sized tray product manufactured by Rembrandt, and the product of Comparative Example 4 was a product manufactured in accordance with Example 2 of Lion's patent publication (Japanese Patent Laid-open No. Hei 10-017,448). After these products were used for 1 hour twice daily for 4 days, the satisfaction index was measured by a sensory test.

In addition, adhesion maintenance was measured after attaching the products to the teeth for 1 hour. The above characteristics of the products were evaluated as to how extent the adhesive strength was maintained for a given one-contact time or how long the trays could be bitten, and were then scored based on the following criteria. 5: very satisfied (no irritation, very strong adhesion to the teeth, fairly excellent adhesion maintenance, no inconvenience in biting tray for given time), 4: satisfied (little or no irritation, slightly strong adhesion to the teeth, good adhesion maintenance, little or no inconvenience in biting tray), 3: average (slight irritation, average adhesion to the teeth, average adhesion maintenance, no large inconvenience in biting tray), 2: unsatisfied (irritation at initial stage, weak adhesion to the teeth, poor adhesion maintenance, slight inconvenience in biting tray), and 1: very unsatisfied (continuous irritation in use, very weak adhesion to the teeth, very poor adhesion maintenance, large inconvenience in biting tray).

TABLE 1

| | Evaluation of convenience in use and safety | | | |
|---|---|---|---|---|
| | Degree of irritation to gums | Wearability | Adhesive strength to teeth | Adhesion maintenance |
| Example 1 | 5 | 4 | 5 | 5 |
| Example 2 | 5 | 4 | 5 | 5 |
| Comp. Example 1 | 3 | 3 | 3 | 2 |
| Comp. Example 2 | 2 | 2 | 2 | 1 |
| Comp. Example 4 | 2 | 3 | 3 | 2 |

As can be seen from Table 1, the largest difference between the products of Examples and Comparative Examples is adhesion maintenance after one-contact time of 1 hour. In the case of the tray type products, it was very inconvenient to continuously bite above 1 hour after adhesion. In particular, the product of Comparative Example 1 was not secured to teeth 1 hour after adhesion and finally separated from teeth by a slight stimulus.

Experimental Example 2

Teeth whitening effect of the products manufactured in Examples 1 to 5 and Comparative Examples 1 to 4 above were measured according to the following procedure.

(1) Preparation of Hydroxyapatite (HAP) Tablet Specimen and Evaluation of Whitening Effects Hydroxyapatite powder was formed into a tablet by means of IR press. The resulting tablet was sintered at a temperature of 1,000° C., molded by an epoxy resin and surface-etched using a strong acid to obtain a tablet specimen. The tablet specimen was dipped in TSB (trypticase soybroth) solution containing tea, coffee, iron and mucin, and dried. This staining procedure was repeated several times over one week. After the staining, the specimen was washed under running water with a mild brushing to remove water-soluble and loosely bound stains. Finally, the specimen was dried at room temperature.

Initial brightness values, L (100 indicates white and 0 indicates black) of the respective specimens were measured by means of a chromameter. The teeth whitening patches prepared in the above Examples 1 to 5 were attached to the specimens which had been soaked in water. The specimens with the attached patches were stored in a thermohydrostat which had been set to conditions similar to those in the oral cavity, which is, at a temperature of 37° C. and a humidity of 95%. After a predetermined time, the patches were detached from the specimens. The detached specimens were washed under running water with a mild brushing and dried at room temperature. L values of the specimens were measured. Difference in the L values before and after attaching the patches, ΔL, was calculated for each patch. The results are shown in Table 2.

TABLE 2

|  | ΔL (One adhesion) | Concentration of hydrogen peroxide in adhesive layer | One-contact time (min.) |
|---|---|---|---|
| Example 1 | 37.8 ± 3.60 | 3% | 200 |
| Example 3 | 32.46 ± 2.02 | 9% | 30 |
| Example 4 | 25.03 ± 2.70 | 6% | 30 |
| Example 5 | 13.86 ± 1.60 | 3% | 30 |
| Comp. Example 1 | 15.60 ± 4.50 | 6% | 30 |
| Comp. Example 3 | 26.03 ± 1.48 | 14% | 30 |

(2) Evaluation of Adhesive Strength to Teeth Before and After Hydration and Contact Time The adhesive strength of the patches to hydroxylapatite as an artificial tooth material was measured using a miniature tensile tester. The results are shown in Table 3 below. The adhesive strength in a dry state was measured after completely drying the sintered hydroxyapatite specimen. The adhesive strength in a wet state was measured after sufficiently adding water to the sintered hydroxyapatite specimen until the specimen was completely wetted and then removing moisture on the surface of the specimen. The wetting conditions were set because the oral cavity is humid but the tooth surface is not wet enough to discover moisture. The adhesive strength of the patches to teeth was obtained by pressing the patches to the specimens at a constant force for a constant time and measuring a force required for detaching the attached patches. The measurement was repeated several times. The results are shown in Table 3.

TABLE 3

| | Adhesive strength to teeth (gmf) | | | | | |
|---|---|---|---|---|---|---|
| | Before hydration | 1 min. after adhesion | 5 min. after adhesion | 10 min. after adhesion | 15 min. after adhesion | 30 min. after adhesion |
| Example 3 | 50.75 | 133.50 | 87.25 | 82.25 | 89.00 | 83.00 |
| Example 4 | 45.50 | 106.50 | 115.00 | 140.00 | 141.75 | 158.00 |
| Example 5 | 38.25 | 120.68 | 135.70 | 138.35 | 137.57 | 135.98 |
| Comp. Example 1 | 39.5 | 33.5 | 26.75 | 22.00 | 20.25 | 18.90 |

As can be seen from Table 3, the dry type patches of Examples 1 to 3 showed at least twice higher adhesive strength in a dry state than in a wet state. On the other hand, there was no significant difference between the adhesive strength of the wet type patch, which is a strip on which gel was coated, of Comparative Example 1 in a wet state and a dry state.

<Usage>

The method for using the dry type patch for teeth whitening according to the present invention is carried out by attaching the patch to the tooth surface to be whitened. The patch consists of a water-soluble section and a water-insoluble section (backing layer). The water-soluble section is directly contacted with the surface of the teeth, and the backing layer acts as a protective wall. As the dry type patch for teeth whitening is hydrated, its flexibility and adhesive strength increase. If the tooth surface is too dry, the patch is initially not attached to the tooth surface. Since the patch can be sufficiently hydrated even in the presence of a small amount of moisture, there is no special problem so long as the tooth surface is not completely dried. In addition, since an excess of moisture can rapidly dissolve the hydrophilic glassy polymer, the adhesive strength of the patch is greatly reduced. Accordingly, it is undesirable to drink a large amount of water or beverage during wearing the patch for teeth whitening.

As apparent from the above description, the patch for teeth whitening according to the present invention is a dry type patch in which a hydrophilic glassy polymer is contained in an adhesive layer. After the dry type patch is attached to the teeth, the glassy polymer provides strong adhesion to the teeth while being hydrated by moisture on the tooth surface and a whitening agent begins to be released. Accordingly, the dry type patch is a safe formulation having no problem in use. In addition, although the dry type patch comes into contact with the hands or other sites, it does not leave any residue, which provides convenience in use. Further, since the dry type patch has strong adhesive strength to the teeth, it is not detached from the teeth during being worn. Furthermore, since the dry type patch has excellent adhesion maintenance to teeth, it can be attached to teeth for a long one-contact time and thus exhibits excellent whitening effects even in the presence of a whitening agent at a low concentration. Moreover, the dry type patch of the present invention is convenient to use and provide excellent whitening effects within a short period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for teeth whitening comprising:
   providing a dry adhesive device for tooth attachment comprising a matrix adhesive layer and a backing layer, wherein the adhesive layer contains a peroxide teeth whitening agent and a hydrophilic glassy polymer as a base polymer selected from polyalkylvinyl ether-maleic acid copolymer, polyvinyl alcohol, polyacrylic acid, poloxamer 407, polyvinyl pyrrolidone-vinyl acetate copolymer, polyvinyl pyrrolidone (PVP), polyquaternium-11, polyquaternium-39, carbomer, hydroxypropylmethyl cellulose, hydroxyethyl cellulose, hydroxypropyl cellulose, gelatin and sodium alginate;
   hydrating the adhesive layer;
   increasing the adhesive strength of said adhesive layer as compared to its dry state prior to its hydration;
   releasing the tooth whitening agent on the enamel layers of the teeth when the adhesive layer is being hydrated;
   maintaining the adhesive strength of the device substantially constant while the teeth whitening agent is being released from the adhesive layer; and contacting the adhesive layer with teeth for a period of about 15 minutes, wherein said hydrophilic glassy polymer is present in amount sufficient to increase the adhesive strength by at least 62% to 260% post hydration.

2. The method according to claim 1, wherein the period of contacting is about 30 minutes.

3. The method according to claim 1, wherein the period of contacting is about 60 minutes.

4. The method according to claim 1, wherein the period of contacting is about 90 minutes.

5. The method according to claim 1, wherein the polymer used in the backing layer comprises a polymer selected from the group consisting of polyvinyl acetate, ethyl cellulose, polymethyl methacrylate, methacryloylethyl betain/methacrylate copolymer, methacrylic acid copolymer, aminoalkylmethacrylate copolymer, cellulose acetate phthalate, shellac or a mixture thereof.

6. The method according to claim 1, wherein the peroxide is used together with a peroxide stabilizer.

7. The method according to claim 1, wherein the peroxide stabilizer is one or more compounds selected from the group consisting of alkylaryl sulphonates, alkyl sulphonates, alkyl carboxylates, alkyldiphenyloxide disulphonates, sorbitan monolaurate, sorbitan monopalmitate, sorbitan monostearate, sorbitan monooleate, sorbitan trioleate and polyoxyethelene sorbitan fatty acid esters.

8. The method according to claim 1, further comprising a polyphosphate for whitening effect enhancement.

9. The method according to claim 8, wherein the polyphosphate is at least one compound selected from tetrasodium pyrophosphate, sodium acid pyrophosphate, sodium hexametaphosphate, sodium tripolyphosphate, sodium potassium tripolyphosphate, tetrapotassium pyrophosphate and acidic sodium metapolyphosphate.

10. The method according to claim 1, wherein the adhesive layer thickness is about 100 μm and the peroxide concentration in the adhesive layer is between 1-4% by weight.

11. The method according to claim 1, wherein the adhesive layer thickness is about 150 μm and the peroxide concentration in the adhesive layer is between 1-4% by weight.

12. The method according to claim 1, wherein the adhesive layer thickness is about 200 μm and the peroxide concentration in the adhesive layer is between 1-4% by weight.

13. The method according to claim 1, wherein the adhesive layer thickness is about 60 μm and the peroxide concentration in the adhesive layer is between 4-7.5% by weight.

14. The method according to claim 1, wherein the adhesive layer thickness is about 80 μm and the peroxide concentration in the adhesive layer is between 4-7.5% by weight.

15. The method according to claim 1, wherein the adhesive layer thickness is about 40 μm and the peroxide concentration in the adhesive layer is greater than 7.5% by weight.

16. The method according to claim 1, wherein the adhesive layer thickness is about 50 μm and the peroxide concentration in the adhesive layer is greater than 7.5% by weight.

17. A method for teeth whitening comprising:
providing a dry adhesive device for tooth attachment comprising a matrix adhesive layer and a backing layer, wherein the adhesive layer contains a peroxide teeth whitening agent and a hydrophilic glassy polymer as a base polymer comprising PVP;
hydrating the adhesive layer;
increasing the adhesive strength of said adhesive layer as compared to its dry state prior to its hydration;
releasing the tooth whitening agent on the enamel layers of the teeth when the adhesive layer is being hydrated;
maintaining the adhesive strength of the device substantially constant while the teeth whitening agent is being released from the adhesive layer; and
contacting the adhesive layer with teeth for a period of about 15 minutes, wherein said hydrophilic glassy polymer is present in an amount sufficient to increase the adhesive strength by at least 62% to 260% post hydration.

18. The method according to claim 17, wherein the period of contacting is about 30 minutes.

19. The method according to claim 17, wherein the period of contacting is about 60 minutes.

20. The method according to claim 17, wherein the period of contacting is about 90 minutes.

21. The method according to claim 17, wherein the backing layer comprises a polymer selected from the group consisting of polyvinyl acetate, ethyl cellulose, polymethyl methacrylate, methacryloylethyl betain/methacrylate copolymer, methacrylic acid copolymer, aminoalkylmethacrylate copolymer, cellulose acetate phthalate, shellac or a mixture thereof.

22. The method according to claim 17, wherein the peroxide is used together with a peroxide stabilizer.

23. The method according to claim 22, wherein the peroxide stabilizer is one or more compounds selected from the group consisting of alkylaryl sulphonates, alkyl sulphonates, alkyl carboxylates, alkyldiphenyloxide disulphonates, sorbitan monolaurate, sorbitan monopalmitate, sorbitan monostearate, sorbitan monooleate, sorbitan trioleate and polyoxyethylene sorbitan fatty acid esters.

24. The method according to claim 17, further comprising a polyphosphate for whitening effect enhancement.

25. The method according to claim 24, wherein the polyphosphate is at least one compound selected from tetrasodium pyrophosphate, sodium acid pyrophosphate, sodium hexametaphosphate, sodium tripolyphosphate, sodium potassium tripolyphosphate, tetrapotassium pyrophosphate and acidic sodium metapolyphosphate.

26. The method according to claim 17, wherein the adhesive layer thickness is about 100 μm and the peroxide concentration in the adhesive layer is between 1-4% by weight.

27. The method according to claim 17, wherein the adhesive layer thickness is about 150 μm and the peroxide concentration in the adhesive layer is between 1-4% by weight.

28. The method according to claim 17, wherein the adhesive layer thickness is about 200 μm and the peroxide concentration in the adhesive layer is between 1-4% by weight.

29. The method according to claim 18, wherein the adhesive layer thickness is about 60 μm and the peroxide concentration in the adhesive layer is between 4-7.5% by weight.

30. The method according to claim 17, wherein the adhesive layer thickness is about 80 μm and the peroxide concentration in the adhesive layer is between 4-7.5% by weight.

31. The method according to claim 17, wherein the adhesive layer thickness is about 40 μm and the peroxide concentration in the adhesive layer is greater than 7.5% by weight.

32. The method according to claim 17, wherein the adhesive layer thickness is about 50 μm and the peroxide concentration in the adhesive layer is greater than 7.5% by weight.

33. The method according to claim 1, wherein the hydrophilic glassy polymer comprise PVP or sodium alginate.

34. The method according to claim 33, wherein the PVP has a molecular weight of greater than 500,000.

35. The method according to claim 33, wherein the peroxide is hydrogen peroxide.

36. The method according to claim 35, further comprising sodium acid pyrophosphate.

* * * * *